United States Patent [19]
Parisis et al.

[11] 4,056,349
[45] Nov. 1, 1977

[54] DEVICE FOR MEASURING SLOPE PARAMETERS FOR A MATERIAL CONTAINED INSIDE A CYLINDER ROTATED ABOUT THE AXIS THEREOF

[75] Inventors: Jean Parisis, Haccourt; Roger Rossion, Richelle; Jacques Depoitier, Wanfercee Baulet, all of Belgium

[73] Assignee: Cimenteries C.B.R. Cementbedrijven, Watermael-Boisfort, Belgium

[21] Appl. No.: 592,053

[22] Filed: June 30, 1975

[30] Foreign Application Priority Data

July 1, 1974 Belgium .............................. 0146110

[51] Int. Cl.² .............................................. F27B 9/40
[52] U.S. Cl. .................................... 432/36; 250/357; 432/32
[58] Field of Search ...................... 432/19, 32, 36, 37, 432/51; 250/357

[56] References Cited

U.S. PATENT DOCUMENTS

| 2,674,695 | 4/1954 | Grace, Jr. ............................ 250/357 |
| 3,103,817 | 9/1963 | Ludwig ................................. 432/32 |
| 3,729,181 | 4/1973 | Itoh et al. ............................. 432/37 |

Primary Examiner—John J. Camby
Attorney, Agent, or Firm—Cushman, Darby & Cushman

[57] ABSTRACT

The invention has for its object a device for measuring the slope parameters of a material contained in a cylinder rotated around the axis thereof.

This device, which senses radiations generated by radio-isotopes passing through the cylinder and the material contained therein, comprises means 1 generating the said radiations and means 8a, 8b picking up the latter fitted outside the cylinder in such a manner that, during the rotation thereof, the radiation generated by the radio-isotopes passing through the slope of material 5 in at least two separate locations is sensed in a specific point of the cylinder, as well as means for analyzing the signals received by the means sensing said radiation.

This device is to be used together with a rotating furnace and particularly a cement kiln.

11 Claims, 6 Drawing Figures

DEVICE FOR MEASURING SLOPE PARAMETERS FOR A MATERIAL CONTAINED INSIDE A CYLINDER ROTATED ABOUT THE AXIS THEREOF

This invention has for object a device for measuring slope parameters for a material contained inside a cylinder rotated about the axis thereof, particularly inside a rotating furnace, by sensing radiations generated by radio-isotopes and passing through the cylinder and the material contained therein.

It is known that inside a rotating cylinder containing a material and particularly inside a cement manufacturing rotating furnace, the material occupies inside each right-angled cross-section of said furnace a socalled slope segment. The angle formed between the chord of said segment and the horizontal is called the slope angle. It is known that the mean lengthwise moving speed of the material in the absence of deposits forming a substantial ring, is inversely proportional to the sine of the natural slope angle, the instantaneous throughput in each section being equal to the product of this speed by the segment area. The material slope angle, the mean lengthwise moving speed, the slope thickness given by the segment rise (that is the filling rate) and the instantaneous throughput are the material slope parameters inside a rotating furnace. It is moreover known that when nearing the firing area, the natural slope angle increases substantially due to the starting of agglomerating reactions. In a given section of the furnace at the inlet to the firing area, the natural slope angle is thus a measure of the preparation condition of said material. It is known that similar phenomenons occur inside similar apparatus such as rotating furnaces for agglomerating ores, furnaces for light aggregates etc. It is of course impossible to determine through visual examination of the slope, the local material throughputs which flow from upstream in the furnace or the preparation rate of said material as it enters the firing zone. A visual determination of the firing rate is possible but at the material outlet from the clinkerizing zone, that is too late to still take an effective action. In the present conditions of the art, it is thus impossible to take into consideration the parameters relating to the slope angle and the slope thickness of the material to use same as regulating means for compensating beforehand a variation of the material flow towards the firing zone or a variation in the preparation condition as the material enters said zone.

It is known presently in the art of the rotating furnaces used for cement manufacturing, to make use of a measuring device as defined above which comprises a fixed radioactive source and a fixed radiation sensor which are so arranged that the radiation transmitted and received go through the furnace walls to the exclusion of the material flowing through said furnace, said device allowing to measure in a particular location of said furnace the thickness of the metal sheet, the refractory lining and the crust formed thereon. There is also known in that same art of rotating furnaces for cement manufacturing, a measuring device of the type defined above which is used to determine the presence or the absence of material inside a furnace and which comprises a fixed radioactive source and a fixed radiation sensor which are so arranged that the radiation goes through the material, this latter measuring device which also allows to determine the material thickness where the radiation goes through same, having the drawback of not allowing to determine any of the above parameters.

The invention has for object to obviate this drawback and to provide a measuring device which allows to locate the slope chord and therefrom the slope angle for a material contained inside a cylinder and more particularly a rotating furnace, the chord of that segment formed by the material slope, the means moving speed of said material inside the cylinder and the instantaneous material throughput therein. With this device according to the invention, there is obtained an actual advance measure of the clinker firing rate at the outlet from the furnace and it is thus possible to act in advance on the usual operating parameters, such as the fuel flow rate, the furnace rotating speed, etc.

For this purpose according to the invention, said device comprises means generating said radiation and mean picking up said radiation which are arranged inside the cylinder in such a way that during the rotation thereof, the radiation from the radio-isotopes which go through the material slope in two separate locations at least are sensed in a determined location along the cylinder, as well as means for analizing the signals received by the means sensing said radiation.

In an embodiment of the invention, the device is so arranged that the radiation generated by the radio-isotopes which go through the material slope in two separate locations at least is sensed during one cylinder revolution.

In another embodiment of the invention, said means are so arranged that the sensing of the radiation from the radio-isotopes occur in a plane at right angle to the cylinder axis.

In an advantageous embodiment of the invention, said means comprise at least one fixed radioactive source and at least two fixed sensors which are located relative to the radioactive source in such a way that the radiations sensed simultaneously by the sensors always go through the material slope, the sensors being located at the same distance from a plane going through the source and the cylinder axis.

In a particularly advantageous embodiment of the invention, said device comprises a third fixed sensor which is arranged relative to the radioactive source in such a way that the radiation sensed by said third sensor at the same time as the radiations sensed by both other sensors does not go through the material slope, said means being so arranged that the signals received by said third sensor be analized relative to those signals received by both other sensors.

Other details and features of the invention will stand out from the description given below by way of non limitative examples and with reference to the accompanying drawings, in which.

In the various figures, the same reference numerals pertain to similar elements.

Figures 1, 2:
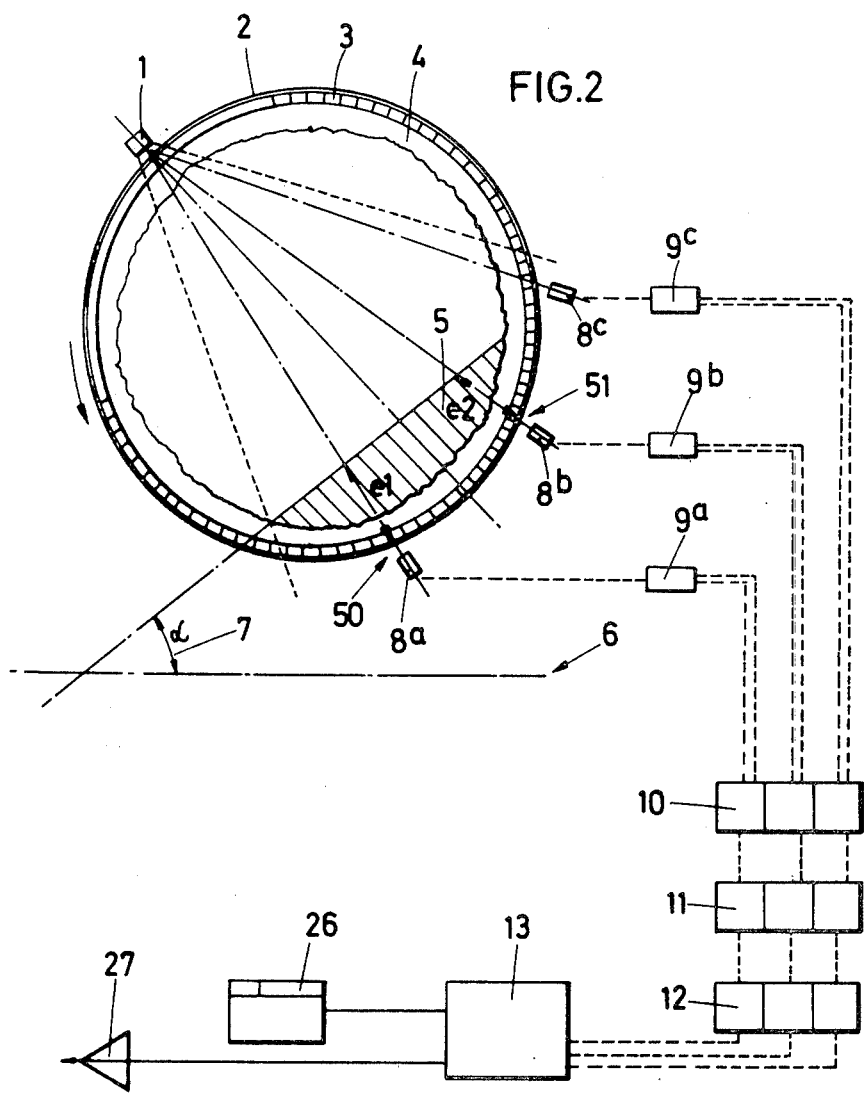
FIG. 1 is a diagrammatic elevation view of a cement-manufacturing rotating furnace provided with a measuring device according to the invention.
FIG. 2 is a diagrammatic view in section along lines II—II in FIG. 1, of the measuring device according to the invention associated with a computing unit for processing the data received from the sensors and for controlling automatically the furnace fuel flow rate.

The rotating furnace shown in FIG. 1 is provided with a measuring device 1' according to the invention, which is arranged in such a position that it lies at the beginning of the furnace clinkerizing zone and it allows through the material slope angle inside the furnace in this location, to sense variations in the material preparation condition as said material enters said clinkerizing zone, at a time when it is still possible to act notably on the furnace temperature, to improve the product quality. Said device 1' comprises means known per se and which have not been shown, which allow to select the position thereof along a direction in parallel relationship to the furnace axis.

The measuring device 1' shown in FIG. 2 comprises a strong radioactive source housed inside a protecting housing 1 which is fixed and arranged adjacent the furnace wall 2 in a location diametrically opposite to the material slope 5, said source generating a gamma-ray bundle which can through the complete furnace inclusive the material slope, said furnace being comprised of a steel tube 2 which is protected inside by a layer of firebricks 3 to which can moreover adhere a crusting 4 with a varying thickness.

According to the furnace rotation direction, the material bed or slope 5 forms relative to a horizontal line 6 an angle 7 which varies with the preparation rate of the product to be clinkerized. On the side of the material slope 5, three sensors 8a, 8b, 8c are arranged adjacent the furnace wall 2 so as to sense the radiation from source 1. The sensors 8a and 8b are so arranged as to capture simultaneously the radiations passing at all time through the material slope and thus to sense in two separate locations 50 and 51 the changes in thickness $e1$ and $e2$ to be able to sense the changes in the sloping material thickness at the level of the sensors and thus to localize the chord of said slope. The sensor 8c is arranged in a location where the material slope cannot come between said sensor and source 1.

Said sensors 8a, 8b, 8c if necessary, are suitably shielded from the furnace heat radiation, for instance by means of a water-jacket, and from the cosmic and secondary radiations, for example, by means of a thick-walled lead cylinder. Said sensors are electrically connected to a computing unit 13 through elements 9 to 12 known per se in such computing installations, said elements being comprised of an impedance-matching pre-amplifier 9, a stabilized DC high-voltage power unit 10, a pulse-counting and integrating unit 11, with a conversion to an analog signal proportional to the sensed radiation, the integrating time of which if stable signals are required, should be at least equal to the furnace revolution period, and an impressed-current voltage converter 12 with galvanic separation for transmitting the signals to some remote location such as an analog or digital computer 13.

Figure 6:
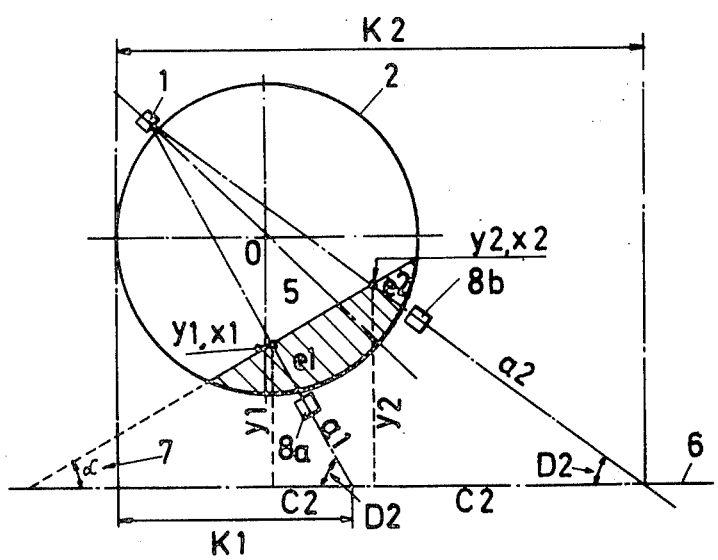
FIG. 6 is a diagrammatic view showing those elements required to determine the material slope angle and which are determined by a measuring device as shown in FIG. 2.

From the signals provided by the three sensors 8a, 8b, 8c and from the known formula for photon-flux absorption (given hereinafter - see FIG. 6), there results:

$$\phi_1 = \frac{\phi_0 \cdot B \cdot e^{-b}}{4 a^2} \quad (1)$$

$\phi_O$: number of photons generated by the radioactive source B: steel diffusion coefficient on the sensor side $c^{-b}: e^{-b2} \times e^{-b3} \times e^{-b4} \times e^{-b5}$ (elements designated by reference numerals 2 to 5 : see FIG. 2)

$b2$ to $b5$ : absorption coefficients due to the different materials through which the radiation passes ($b = k \times$ thickness)

$a$ = spacing source-sensor $\phi_1$ : number of photons captured by the sensor

For a given sensor, various constants can be grouped as a coefficient in which will also intervene the cross-section and the efficiency of said sensor.

$$\phi_1 = K.e^{-(b3 + b4 + b5)} \quad (2)$$

In relation (2), $b4$ can be replaced by the brick equivalent thereof and the total $b3 + b4$ becomes $b'3$.

In the case of sensor 8a,
$$\phi_{1a} = K_a e^{-(b'3 + b5)} \quad (3)$$

and $$\phi_{1c} = K_c e^{-b'3} \quad (4)$$

in the case of sensor 8c. The computing unit determines the material slope thickness at the level of sensors 8a and 8b, the third sensor 8c comprising actually the measure reference which allows to take into consideration the changing thickness of the crusting 4 or the wearing down of the refractory lining 3, these latter elements intervening twice in the radiation absorption. Once known the respective positions of sensors 8a and 8b and the material slope thickness in said separate locations, the solving of usual geometry formulae allows to determine the coordinates of the crossing points of the captured radiations and the material slope and therefrom the angular coefficient of said material slope which is the measured amount looked for, the procedure to obtain said measured amount being given hereinafter:

Determination of the Sloping Material Thickness at the Level of the Sensors

The relation giving the brick-crusting thickness is deduced from (4) (see the formula for absorption):

$$b'3 = \ln \frac{K'_c}{\phi_{1c}} \quad (5)$$

in which $\phi_{1c}$ is the signal at sensor 8c.

The relation for the brick-crusting-slope thickness is deduced from (3):

$$b'3 + b5 = \ln \frac{K'_a}{\phi_{1a}} \quad (6)$$

in which $\phi_{1a}$ is the signal at sensor 8a.

The relation for the sloping material thickness at the level of sensor 8a is: (6) - (5):

$$b5 = \ln \frac{K'_a}{\phi_{1a}} - \ln \frac{K''_c}{\phi_{1c}} \quad \text{that is } \ln K''' \frac{\phi_{1c}}{\phi_{1a}}$$

$$e_1 = \frac{b5}{k5}$$

P.S.: — K'', the measure for the crusting (sensor 8c) is referenced to the measuring conditions of sensor 8a (different positions etc.)

Computing the Coordinates of Said Crossing Points: (y1, x1) and (y2, x2) (see FIG. 6)

$$y2 = (a2 + e2) \sin D2$$

$$x2 = K2 - C2$$

$$= K2 - (y2 \cotg D2)$$

$$y1 = (a1 + e1) \sin D1$$

$$x1 = K1 - (y1 \cotg D1)$$

Computing the Angular Coefficient for α

$$\tg \alpha \ (7) = \frac{y2 - y1}{x2 - x1}$$

| Known values | |
|---|---|
| a2 | a1 |
| D2 | D1 |
| K2 | K1 |
| Measured values | |
| e2 | e1 |

Said measure is either recorded in the case of a manual control to allow the firing operator to follow the change thereof and if need be, to act upon the furnace operating parameters and notably on the fuel flow rate, or transmitted as anticipating magnitude, for example, to the analog or digital regulator 26 controlling the fuel flow rate 27 in the case of an automatic operation of said furnace.

It is well understood that the number of sensors can be increased which improves the accuracy of the measuring while allowing the validation of the signals from the sensors. It would also be possible to feed directly the signals from the sensors to a digital computer.

Figure 3:
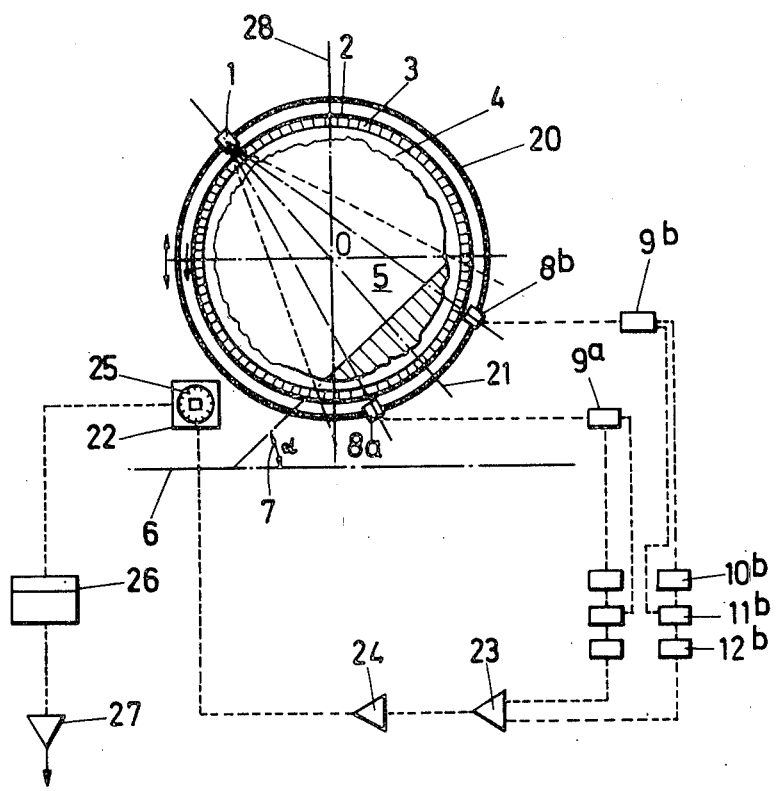
FIGS. 3, 4 and 5 are views similar to FIG. 2 showing another embodiment of the measuring device and the computing unit shown in FIG. 2.

The measuring device according to the invention and shown in FIG. 3 is another embodiment of the above-described device. The measuring of the material slope angle is obtained directly from the position of a ring in co-axial relationship with the furnace, the rotation of which is so controlled as to bring the ray bundle generated by source 1 substantially at right angle to the material slope, substantially in the centre thereof.

This device comprises a ring 20 which surrounds the furnace 2. Said ring 20 bears on the one hand, the radioactive source inside the protecting container 1 thereof and on the other hand, diametrically opposite to source 1, two sensors 8a and 8b arranged symmetrically relative to the axis 21 that passes through source 1 and the furnace centre 0, the source and the sensors being made fast to the ring 20 in an adjustable way. Said ring 20 is coupled to a servo-mechanism 22 which imparts to said ring an angular displacement so as to locate the symmetry axis 21 of sensors 8a, 8b in the centre of material slope 5 and to follow the changes of said centre. The signals from both sensors 8a, 8b are fed through the components of the above-described measuring chain 9 to 12, to the input of a regulator 23 so as to sense the equality of both signals (zero method) when both sensors 8a, 8b receive the same radiation, that is when there is the same material thickness between sensors 8a, 8b and source 1. The output from regulator 23 operates through the usual position driver 24 of a regulating chain, the servo-mechanism 22 along a rotation direction in relation with the sign of the signal differential at the regulator 23 so as to continuously perform a balancing of both signals from sensors 8a, 8b, the ring position being sensed through an angle transmitter 25 coupled to the servo-mechanism 22.

The measure of the material slope angle thus obtained will as stated above be fed to a recorder, regulator, etc. depending on whether the furnace control is manual or automatic.

The positioning of ring 20 could also be performed in a digital way (pulse counters, computer, etc...)

Figure 4:
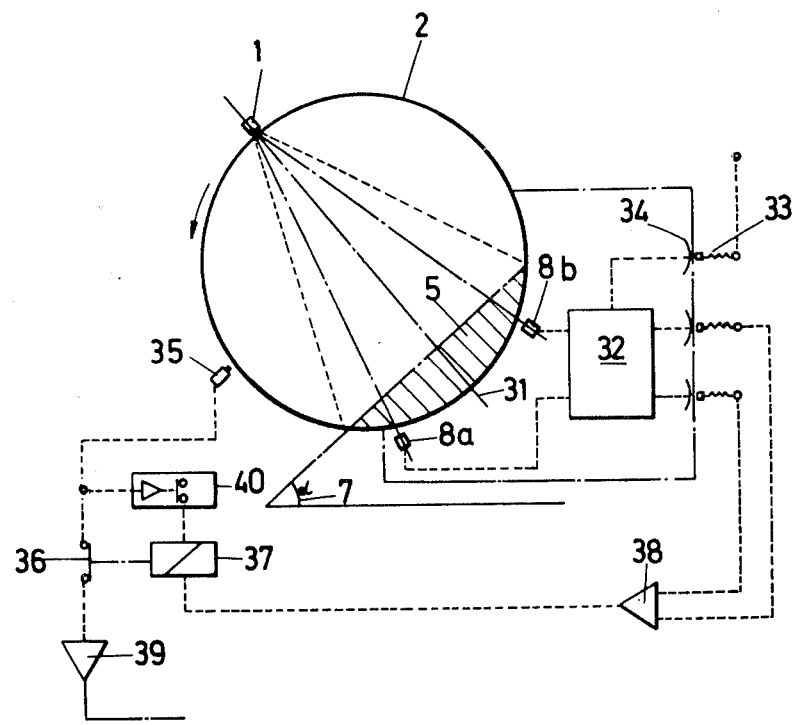

The measuring device according to the invention shown in FIG. 4 is based on the principle of that device shown in FIG. 3. The elements previously fastened to the ring 20 in this latter device are directly made fast to the furnace and the slope angle measure is obtained cyclically.

When the conditions allow such a solution, the radioactive source can be made fast to the furnace 2 as well as two sensors 8a and 8b which are diametrically opposed and equally spaced from a symmetry axis 31 which passes through the furnace axis.

The electronic equipment similar to the one of the device shown in FIG. 1 and associated with the sensors will be contained inside a housing 32 made fast to furnace 2.

The electric supply will be fed through shoes 33 to rings 34 which rotate together with said furnace.

The measuring signals will either be collected also through sliding shoes or transmitted by a radio link. A transmitter 35 senses the furnace angular position. The position of slope angle 7 is determined as in the case of the device shown in FIG. 3 through the zero method. At the moment when the sensor signals are balanced, the information relating to the furnace position is fed to a memory amplifier 39 through a contact 36 of relay 37 energized by zero amplifier 38. Relay 37 is moreover locked through an auxiliary device 40 when the sensors do not lie in the normal zone of the material slope. The measuring thus performed is cyclic, in relation with the furnace rotation period; however the information relating to the position of the slope angle is continuously present by means of the memory amplifier 39.

Reference will be made to the description of the device shown in FIG. 2 for examples of use of said latter measuring.

The description of said three measuring devices has been made in relation with the measuring of the material slope angle, which gives indications as to the degree of preparation of the material entering the clinkerizing zone of a cement-manufacturing rotating furnace.

It is clear that without departing from the scope of this patent, said measuring device can be used to investigate any location in the furnace and even in any equipment comprised of a cylinder rotating about the axis thereof and conveying some material.

The knowledge of other parameters such as the filling rate or the instantaneous material flow rate, can be required. In this case the described measuring devices allow to determine said parameters. Generally the information relating to the total slope-brickcrusting thickness. It will usually be enough to perform the brickcrusting measuring alone to determine through computing the rise of the segment formed by the slope material, that is to determine the furnace filling rate.

Said measuring is already allowed when using the device shown in FIG. 2. In the case of that device shown in FIG. 3, it is possible to make said measuring to locate a third sensor which is influenced by radiation which does not go through the material slope or to operate cyclically ring 20 to make the measuring outside the material slope. In this latter case a storage system for the last angular position of said device gives a temporary substitute measuring signal.

As regards the device shown in FIG. 4, it is sufficient to obtain the signals from the sensors when the slope does not lie between said sensors and the radioactive source.

When the filling rate is known, there can be deduced therefrom the instantaneous material flow rate as the material moving speed inside the rotating furnace fulfills the relation:

$$V = K \phi n \frac{\sin p}{\sin \alpha}$$

in which: K = constant; $\phi$ = cylinder diameter; $n$ = rotation speed; p = furnace slanting are known while $\alpha$ = material slope angle is determined by means of one of said known measuring devices.

The instantaneous material flow rate will thus be the product of the above-mentioned speed by the furnace filling rate.

It must be understood that the invention is in no way limited to the above embodiments and that many changes can be brought therein without departing from the scope of the invention as defined by the appended claims.

Figure 5:
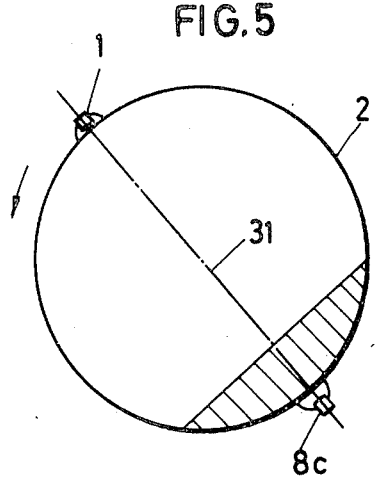

For instance, it would be possible to provide as a variation in the device shown in FIG. 4, a source 1 and a sensor 8c which are fastened to the furnace 2 along the axis 31 that passes through the furnace axis (see FIG. 5), the measuring of the slope thickness being made by means of sensor 8c in at least two separate locations during the sweeping of said slope with the radiation from the radioactive source 1, the measuring of the furnace thickness inclusive the crusting, being made when the material slope does not lie between the source 1 and sensor 8c.

It would further be possible when the device is provided with a multiplicity of sensors, to provide said device with one radioactive source per sensor with a calibrating of said sources.

It would also be possible to provide for the device associated with a rotating cement furnace, to comprise analog or digital means which are so designed as to combine the signals from said analyzing means with other measuring signals, such as for the clinkerizing temperature, the furnace driving moment, the temperature upstream of the furnace clinkerizing zone, the decarbonating activity, etc; said means being so arranged as to combine the signals received from said analyzing means directly and/or as time derivatives and/or as integrated with said other measuring signals. The device advantageously comprises known means for weighting the signals from said analyzing and measuring means as well as adding means connected to the outputs of said weighting means, means for time displacement being also provided between the weighting means and the adding means.

We claim:

1. A device for measuring slope parameters for a loose material contained inside a hollow cylindrical wall which rotated about its axis so that when viewed in transverse cross section the material forms a slope segment in engagement with the inner surface of said wall, said apparatus comprising a radioactive source generating a stream of penetrating radiation; means supporting said radiation generating means adjacent the exterior of said cylindrical wall at a location opposite the slope segment in a position in which the stream of radiation passes through said wall and through at least two circumferentially spaced-apart portions of the slope segment of material; separate means for sensing the radiation passing through each of the two portions and generating signals in accordance with the sensed radiation; and means for analyzing the signals from said sensing and signal generating means.

2. Apparatus as in claim 1 wherein said sensing means operate during one revolution of said cylindrical wall.

3. Apparatus as in claim 1 wherein said sensing means are disposed in a plane which is at a right angle to the axis of said cylindrical wall.

4. Apparatus as in claim 1 wherein there are two sensing means which are located at the same distance from a plane through said radioactive source and the axis of said cylindrical wall.

5. Apparatus as in claim 4, which comprises a third fixed sensing means for sensing radiation, simultaneously with said two sensing means, which does not go through the material slope, and wherein said analyzing means analyzes signals from said third sensing means relative to those signals received by both other sensors.

6. Apparatus as in claim 4, in which the sensors are electrically coupled to an analog or digital computing unit which continuously determines the slope thickness at the level of said sensors.

7. Apparatus as in claim 1 wherein said radioactive source is movable relative to said cylindrical wall, the spacing between said radioactive source and the axis of the cylindrical wall remaining constant, and wherein at least two identical sensors are fixed relative to said radioactive source and arranged symmetrically relative to the axis of said radioactive source axis which crosses the axis of said cylindrical wall.

8. Apparatus as in claim 7, in which the radioactive source and both said sensors are carried by a ring in co-axial relationship with said cylindrical wall, and means to impart to said ring a rotating movement about the axis thereof so as to retain said radioactive source axis substantially at right angle to the material slope.

9. Apparatus as in claim 9 wherein the radioactive source and the sensors are adjustable along said ring.

10. Apparatus as in claim 8, in which said means to rotate said ring comprise a computing unit coupled to the sensors and which analyzes the signals from said sensors, a regulator associated with the computing unit and sensing the equality of both signals when both sensors receive identical radiations, a position drive associated with the regulator, a servo-mechanism for controlling the ring which is operated by said position drive determining the ring rotation direction about the axis thereof according to the sign of the differential of those signals sensed by the regulator and an angle transmitter coupled to the servo-mechanism to sense the ring position.

11. Apparatus as in claim 1 wherein said radioactive source is fixed to said wall and wherein at least one sensing means is fixed to said cylindrical wall, and control means for said one sensing means for collecting signals therefrom at the moment when the radiation generated by the source goes through the material slope.

* * * * *